United States Patent
Hendler et al.

(10) Patent No.: US 6,506,166 B1
(45) Date of Patent: Jan. 14, 2003

(54) APPARATUS AND METHOD FOR ACQUISITION AND RETRIEVAL OF RESECTED BIOLOGICAL SPECIMENS

(76) Inventors: Shoshan Hendler, 10 Jerico Street, Holon 58549 (IL); Mosht Maroko, 16 Arinzorov Street, Hon HaSharon 45203 (IL)

( * ) Notice: Subject to any disclaimer, the term of this patent is extended or adjusted under 35 U.S.C. 154(b) by 0 days.

(21) Appl. No.: 09/763,998
(22) PCT Filed: Aug. 23, 1999
(86) PCT No.: PCT/IL99/00461
§ 371 (c)(1), (2), (4) Date: Feb. 26, 2001
(87) PCT Pub. No.: WO00/12011
PCT Pub. Date: Mar. 9, 2000

(30) Foreign Application Priority Data

Aug. 27, 1998 (IL) .................................................. 125965

(51) Int. Cl.⁷ ................................................. A61B 5/00
(52) U.S. Cl. ...................... 600/562; 606/115; 606/123; 604/319
(58) Field of Search ........................ 600/562, 564–567; 606/114, 115, 123; 604/319

(56) References Cited

U.S. PATENT DOCUMENTS

| | | | |
|---|---|---|---|
| 3,495,593 A | * | 2/1970 | Snyder ........................ 606/115 |
| 3,765,408 A | * | 10/1973 | Kawai ......................... 128/303 |
| 5,176,687 A | | 1/1993 | Hasson et al. |
| 5,196,003 A | | 3/1993 | Bilweis |
| 5,215,521 A | | 6/1993 | Cochran et al. |
| 5,279,548 A | | 1/1994 | Essig et al. |
| 5,417,697 A | | 5/1995 | Wilk et al. |
| 5,465,731 A | | 11/1995 | Bell et al. |
| 5,480,404 A | | 1/1996 | Kammerer et al. |
| 5,647,372 A | | 7/1997 | Tovey et al. |

FOREIGN PATENT DOCUMENTS

| WO | WO 97/17021 | 5/1997 |
|---|---|---|
| WO | WO 97/26828 | 7/1997 |

* cited by examiner

*Primary Examiner*—Max Hindenburg
(74) *Attorney, Agent, or Firm*—Scully, Scott, Murphy & Presser

(57) ABSTRACT

The invention provides a vacuum mouthpiece (2) for the acquisition and retention of resected biological specimens for retrieval from a body cavity, the mouthpiece being attached to a first tubular member (4) connectable to a vacuum source and having an active surface including at least one opening communicating with the first tubular member; the mouthpiece (2) being made of an elastically resilient material and having, in a free state, an outside diameter larger than the inside diameter of a second tubular member (24) into which it is insertible by elastic deformation. The invention further provides a closable pouch (20) for the entrapment and retrieval of a resected biological specimen from a body cavity, and a laparoscopic system and method utilizing the above.

15 Claims, 3 Drawing Sheets

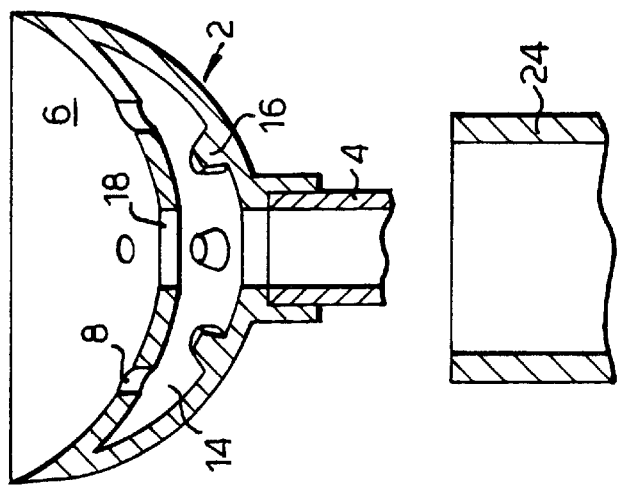
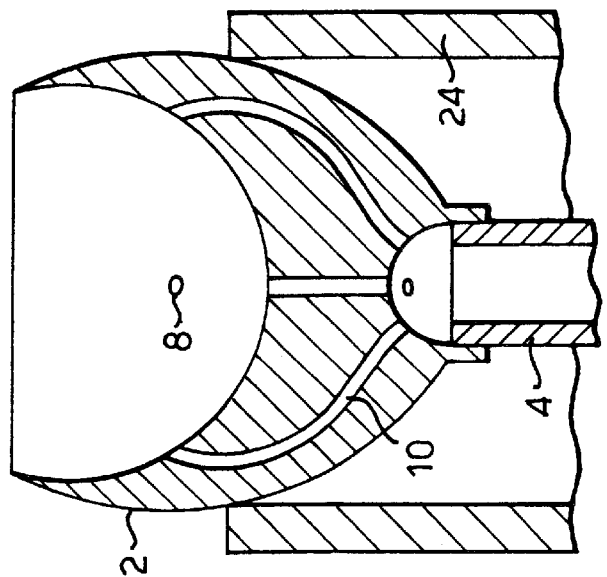
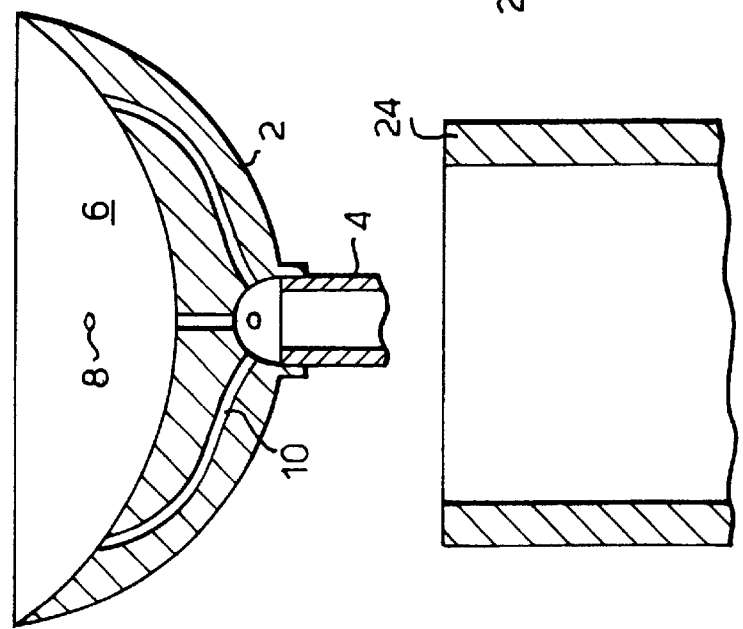

APPARATUS AND METHOD FOR ACQUISITION AND RETRIEVAL OF RESECTED BIOLOGICAL SPECIMENS

FIELD OF THE INVENTION

The present invention relates to an apparatus and method for acquisition and retrieval of resected biological specimens. More specifically, the present invention is concerned with a vacuum mouthpiece for the acquisition and retrieval of resected biological specimens from a body cavity, a self-closing pouch for entrapment and retrieval of resected biological specimens from a body cavity, and a laparoscopic system incorporating such a mouthpiece and such a pouch.

BACKGROUND OF THE INVENTION

Laparoscopy, also known as "keyhole surgery," is today increasingly complementing and even replacing conventional surgery, especially in the abdominal region, for resection and removal of diseased organs such as a gall bladder, ovaries, or diseased parts of such organs, cysts, and the like. The small incisions required for laparoscopic procedures minimize skin scarring, reduce the risk of infection, and greatly speed up would healing.

Laparoscopic devices for the removal of resected specimens are known, most of which are based on the use of a pouch and propose ways of closing that pouch with the specimen inside it, such as a drawstring thread (U.S. Pat. Nos. 5,647,372 and 5,465,731) as well as grasping means to control the pouch edges, but do not address the cardinal issue of getting hold of the resected specimen, putting it into the pouch, and withdrawing it from the body cavity.

U.S. Pat. No. 5,480,404 teaches a belt-like loop with a flexible pouch which enables the scooping up of the specimen, closing the pouch and removing it from the body cavity. This disclosure too, only partially resolves the issue of "catching" the specimen, and does not deal satisfactorily with the withdrawal of the specimen from the body cavity.

Instead of a pouch, U.S. Pat. No. 5,176,687 uses a flexible membrane which has a collapsed and an expanded state, but it does not deal with the retrieval of the specimen.

U.S. Pat. No. 5,215,521 discloses an envelope sheath to entrap the resected specimen as well as a morcellator allowing for safe morcellation of the specimen, and provides both for the catching and the retrieval thereof, but the apparatus and auxiliaries described are highly complex and require the services of two experienced laparoscopists.

U.S. Pat. No. 5,279,548 teaches a method for use in a peritoneal or pelvis surgery, in which a funnel-like membrane introduced into the body cavity is positioned vertically below the organ to be resected, allowing the resected tissue to fall into the membrane.

WO 97/17021 discloses a device for retrieving tubular parts such as stents from blood vessels. The gripping members of the device are provided with hooked ends adapted for engaging the stent.

U.S. Pat. No. 5,196,003 teaches a surgical instrument for endoscopic surgery having an elastically deformable suction cup communicating with a rubber bulb, whereby a suction effect can be applied to retain resected tissues.

WO 97/26828 discloses a laparoscopic instrument for handling parencynmatous and cavum organs. The device is provided with a funnel-like suction cup tiltably articulated to a tubular member and serving to retrieve resected tissue. The assembly is a single unit, and the suction cup cannot be moved independently of the retrieval member.

U.S. Pat. No. 5,417,697 teaches a polyp retrieval assembly comprising a cauterizing loop and a cup-shaped web member for retrieving resected tissue. The assembly is a single unit, and the web member cannot be moved independently of the retrieval member.

It is thus one of the objects of the present invention to provide a mouthpiece introducible into a body cavity for acquisition and retention of a resected biological specimen by vacuum suction.

It is a further object of the present invention to provide a pouch that is self-closing after being introduced into a body cavity, thereby entrapping a resected biological specimen for retrieval.

It is yet another object of the present invention to provide a relatively simple laparoscopic device that facilitates the vacuum capture and retention of a resected biological specimen, its entrapment in a self-closing pouch and its retrieval, and that can be operated by a single surgeon with no more than moderate experience in laparoscopy.

According to the invention, there is therefore provided a device for the acquisition and retention of resected biological specimens for retrieval from a body cavity, said device comprising a bowl-shaped mouthpiece made of an elastically resilient material; a first tubular member having a distal end connected to said mouthpiece and a proximal end connectable to a vacuum pump; characterized in that a plurality of openings are distributed over said mouthpiece, said openings leading to the distal end of said first tubular member, thereby facilitating the retention and retrieval of resected biological specimens by vacuum suction.

The invention also provides a closable pouch for the entrapment and retrieval of a resected biological specimen from a body cavity, said pouch comprising pliable, pre-shaped, membranous material attached at selected points substantially along meridian lines, to a plurality of pre-shaped, finger-like elements, said elements having distal ends and proximal ends, the proximal ends of said finger-like elements being connected to a tubular member slidably located inside an outer tubular member, characterized in that said finger-like elements exhibit different responses in different states, a first state response in which the distal ends of said finger-like elements flex away from each other, thereby causing the pouch to open and to engulf and entrap said specimen, and a second state response in which the distal ends of said finger-like elements flex toward each other, thereby causing the pouch to close, thereby retaining said specimen for retrieval.

The invention further provides a laparoscopic system for acquisition and retrieval of resected biological specimens, said system comprising at least three telescoping tubular members having distal and proximal ends, including an outer tubular member, an inner tubular member defining with said outer tubular member an annular space and being connectable at its proximal end to vacuum-producing means, and an intermediate tubular member slidably fitting said outer tubular member; a bowl-like mouthpiece having a front face and a rear face, for capturing and retaining a resected specimen, said mouthpiece being connected at its rear face to the distal end of said inner tubular member and being made of an elastically resilient material, said mouthpiece having a diameter in a non-deformed state exceeding the inside diameter of said outer tubular member but fitting into the distal end of said outer tubular member by elastic deformation; a plurality of finger-like elements fixedly connected to the distal end of said intermediate tubular member; a pouch made of pliable, membraneous material fixedly attached at a plurality of points to said plurality of finger-like elements; characterized in that, in the non-active, telescoped state of said system, said pouch, connected to said plurality of finger-like elements, is collapsed and disposed inside said annular space behind the rear face of said mouthpiece, and in the active state of said system, when said intermediate tubular member is pushed out of the outer tubular member, the distal ends of said finger-like elements first flex away from each other, thereby causing the pouch to open and to engulf said mouthpiece, and thereafter, the distal ends of said finger-like elements flex toward each other, thereby causing the pouch to close, entrapping and retaining said specimen for retrieval.

The invention still further provides a method for acquisition and retrieval of resected biological specimens, using the laparoscopic system described above, the method comprising the steps of introducing the distal end of the telescoped device into the body cavity; pushing out the inner tubular member, thereby removing the mouthpiece from the outer tubular member and causing said mouthpiece to assume its full diameter; actuating the vacuum-producing means and moving mouthpiece to a location in close proximity to the specimen to be resected, causing the resected specimen to cling to said mouthpiece; pushing out the intermediate tubular member, thereby causing the distal ends of finger-like elements to emerge from the annular space between the outer tubular member and the inner tubular member, said finger-like elements carrying along and opening up the pouch attached to them for engulfing the specimen retained by said mouthpiece; allowing the distal ends of said finger-like elements to close over said mouthpiece, thereby closing the pouch over said specimen, and withdrawing the device from the body cavity.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

FIG. 1 is an enlarged, cross-sectional view of a first embodiment of the vacuum mouthpiece according to the invention in its free state;

FIG. 2 is a similar view of the embodiment of FIG. 1 when elastically deformed to fit the tubular member;

FIG. 3 is an enlarged cross-sectional view of a substantially hollow embodiment of the vacuum mouthpiece according to the present invention;

DETAILED DESCRIPTION OF PREFERRED EMBODIMENTS

Figure 4:
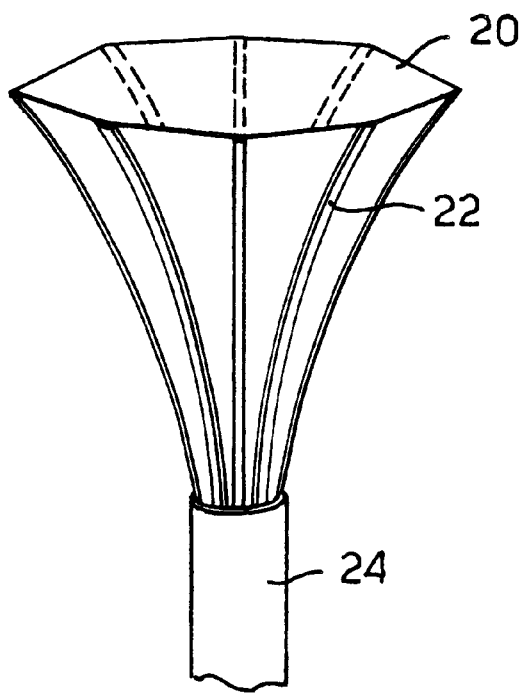
FIG. 4 is a perspective view of the open pouch.

Referring now to the drawings, there is seen in FIG. 1 a first embodiment of a vacuum mouthpiece 2 according to the invention in its fully expanded state. Mouthpiece 2 is attached, e.g., by adhesive bonding, to a first tubular member 4 connectable to a vacuum pump (not shown). Mouthpiece 2 has a bowl-like shape and is made of an elastically resilient material such as synthetic rubber or the like. Active surface 6 is concave and is provided with a plurality of openings 8 which, via ducts 10, communicate with a first tubular member 4. Also seen is a second tubular member 24 into which, as shown in FIG. 2, mouthpiece 2 can be inserted by elastic deformation.

A second embodiment of the mouthpiece, shown in FIG. 3, is substantially hollow. To prevent the collapse of hollow space 14 under the effect of underpressure produced by the above-mentioned vacuum source, which collapse would affect the communication of peripheral openings 8 with the vacuum source, there are provided a plurality of protrusions 16 integral with either he bottom and/or the roof of hollow space 14, that will limit the amount by which the roof and the bottom of space 14 may approach one another. Protrusions 16 could also have the shape of crenellated ribbing that would also enhance the stiffness of mouthpiece 2.

Further seen in FIG. 3 is a central opening 18 in active surface 6, which is much larger than the peripheral openings 8 and which facilitates the passage therethrough of various implements, such as a morcellator or a suction needle.

FIG. 4 shows a pouch according to the invention, in the open state. Pouch 20 is made of a pliable, membranous material, is advantageously pre-shaped like the canopy of an umbrella, and is fixedly attached, e.g., by adhesive bonding, at selected points along substantially meridianal lines, to a plurality of finger-like elements 22. Since the purpose of pouch 20 is first to engulf and then to enclose the resected specimen, e.g., a cyst, means must be at hand to first spread the pouch open to enable it to entrap the specimen, and then to close the pouch, retaining the specimen for imminent retrieval.

Therefore, the elements 22 are constituted by any suitable material or a combination of materials, e.g., plastic, metal or plastic-coated metal. The elements 22 are pre-shaped and adapted to assume a first state in which they flex outwardly and a second state in which they flex inwardly towards each other.

Figure 5:
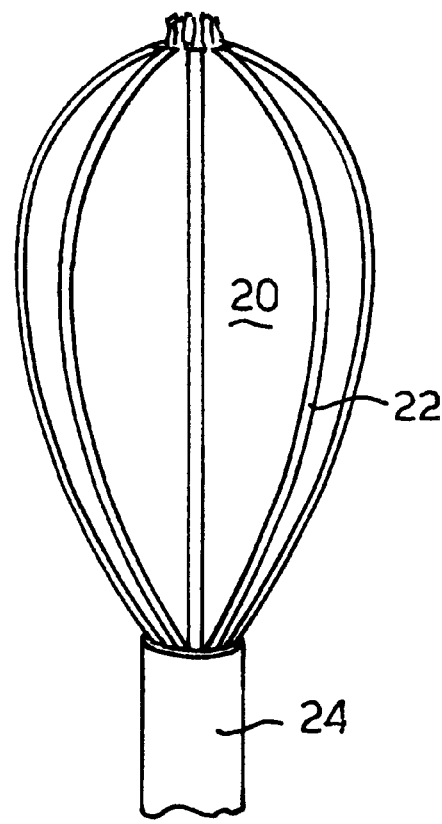
FIG. 5 is a perspective view of the closed pouch.

The finger-like elements advantageously may be made of a shaped-memory alloy, i.e., an alloy which "remembers" one or more shapes imparted to it at one or more predeterminable temperatures, and which reverts to those shapes whenever it is subjected to those temperatures. Such alloys are commercially available, for instance, Nitinol, a nickel-titanium alloy, or the like. Hence, in operation, when the elements 22 are exposed to a first temperature, e.g., room temperature, or a lower temperature obtained by cooling, they are caused to flex outwardly, i.e., to flare open. Since pouch 20 is attached to the elements 22, the pouch is likewise caused to open, as shown in FIG. 4. When the elements 22 are exposed to a second, higher temperature, e.g., body temperature, or heated, however, they are caused to flex inwardly towards each other. This change of shape of the elements is, of course, also imparted to pouch 20, causing it to close as shown in FIG. 5. The higher (transition) temperature could also be effected by passing a weak electric current through elements 22, thereby achieving better control of the procedure.

Figure 6:
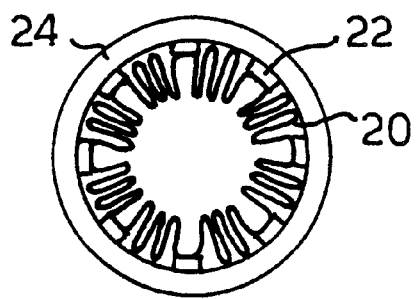
FIG. 6 is a top view showing a tubular member accommodating the finger-like elements and the folded pouch prior to their use.

Prior to use, finger-like elements 22 and pouch 20 are retained in a tubular member 24 as seen in the top view of FIG. 6, showing pouch 20 folded in its fully collapsed condition.

FIGS. 7–11 illustrate a laparoscopic system for acquisition and retrieval of resected biological specimens. As this system also incorporates the vacuum mouthpiece and pouch illustrated in FIGS. 1–5, reference will be made to some of these Figures in discussing the laparoscopic system according to the invention.

Figure 7:
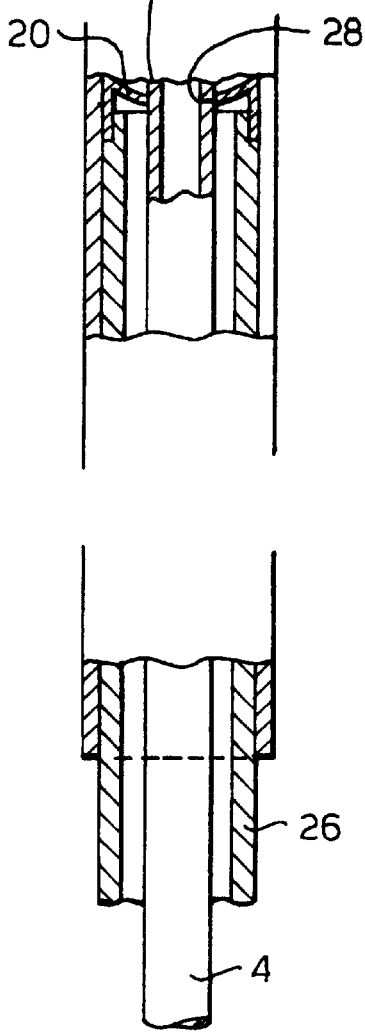
FIG. 7 is an enlarged, partial cross-section of the laparoscopic system according to the present invention in its non-active, fully telescoped state.

Referring now to FIG. 7, there is seen an outer tubular member 24, the distal end 25 of which is designed to be introduced into a body cavity from which a previously resected specimen is to be retrieved. Introduction is effected in a per se known manner, using a trocar. The outside diameter of member 24 is of an order of 10 mm.

Further seen is an inner tubular member 4 of a length exceeding the length of member 24 and connectable at its proximal end to a vacuum pump (not shown). To the distal end of tubular member 4 is fixedly attached a vacuum mouthpiece 2 made of an elastically resilient material such as synthetic rubber or the like. In its free state as shown in FIG. 3, its outside diameter is much larger than the inside diameter of tubular member 24.

Freely sliding inside outer tubular member 24, there is arranged an intermediate tubular member 26 which also projects beyond the proximal end of member 24. To the distal end of member 26 are fixedly attached, e.g., by welding or brazing, a plurality of finger-like elements 22 which cause pouch 20 to be first spread open and then, after it has engulfed the specimen to be retrieved, to close with the specimen inside, as explained above.

Figure 8:
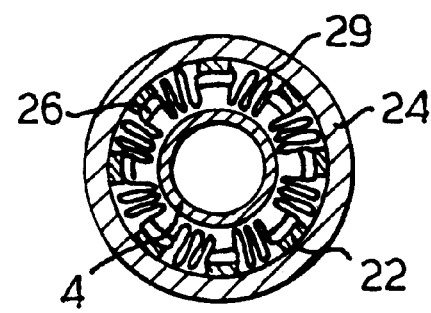
FIG. 8 is a more enlarged view in cross-section along plane XIII—XIII of the system of FIG. 7.

As further seen in FIG. 7, pouch 20 is provided at its center with an opening 28, through which passes tubular member 4. In its initial state, pouch 20 is fully collapsed, i.e., folded, its folds filling the annular space between tubular members 24 and 4, as can be seen in FIG. 8.

Figure 9:
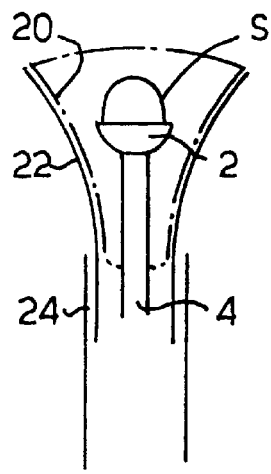
FIG. 9 schematically illustrates the flaring open of the finger-like elements and the resulting opening of the pouch.
Figure 10:
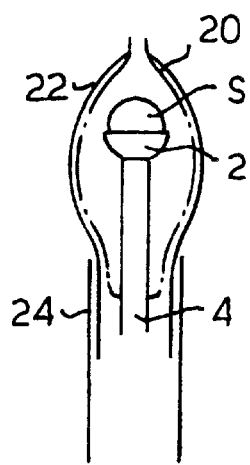
FIG. 10 schematically illustrates the inward flexing of the finger-like elements and the resulting closure of the pouch.

In actual operation, after the distal portion of the device, still in the state depicted in FIG. 7, is introduced into the body cavity using a per se known trocar, inner tubular member 4 is pushed out, thereby releasing vacuum mouthpiece 2 from its confinement in outer tubular member 24. At the same time, the vacuum pump to which member 4 is connected is switched on. Due to the suction effect of the approaching mouthpiece 2, the previously resected specimen will be drawn close and cling to it. More or less simultaneously, intermediate tubular member 26 is pushed out and elements 22, previously restrained by tubular member 24 from assuming their flaring shape, now flare open, thereby opening pouch 20. This situation is schematically illustrated in FIG. 9, showing specimen S clinging to vacuum mouthpiece 2 and finger-like elements 22 flexing outwardly, thereby opening pouch 20, which now surrounds specimen S. The specimen can now be resected through the use of any suitable surgical instrument and the pouch 20 closed to engulf the resected specimen for safe retrieval (FIG. 10). In a case when shaped-memory elements are used, after the elements 22 have been largely exposed to the higher body temperature for a while (or have been electrically heated), they are affected by the high-temperature memory and flex inwardly, thereby closing pouch 20 and thus effectively capturing specimen S.

Figure 11:
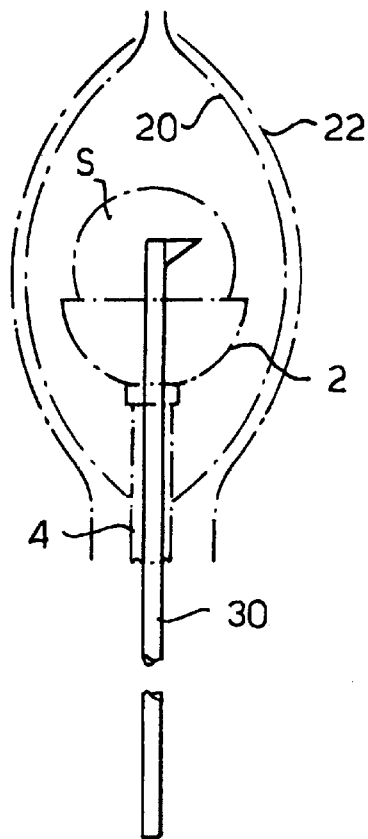
FIG. 11 shows a morcellator used for the fragmentation and liquefaction of solid specimens.

Further proceedings depend on the nature of the specimen. Fairly low-viscosity specimens, such as exudates, can be drawn off by a suction needle introduced into pouch 20 via opening 18 in mouthpiece 2, or even by the latter itself. More solid specimens must be liquefied, which is best done with the aid of a morcellator 30, as shown in FIG. 11. This implement is introducible into closed pouch 20 via opening 18 in mouthpiece 2 and, driven at high speed by any suitable drive means, acts like a blender. Closed pouch 20 prevents spilling of the liquid into the abdominal cavity. The thus liquefied specimen can then be drawn off, either by the above-mentioned suction needle or directly by mouthpiece 2.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for the acquisition and retention of resected biological specimens for retrieval from a body cavity, said device comprising:

a bowl-shaped mouthpiece (2) made of an elastically resilient material;

a first tubular member (4) having a distal end connected to said mouthpiece (2) and a proximal end connectable to a vacuum pump;

characterized in that a plurality of openings (8) are distributed over the entire mouthpiece (2), said openings (8) leading to the distal end of said first tubular member (4), thereby facilitating the retention and retrieval of resected biological specimens by vacuum suction.

2. The device as claimed in claim 1, characterized in that said mouthpiece (2) is made of substantially solid material and comprises a plurality of ducts (10) inside said solid material, said ducts (10) leading from said openings (8) to said distal end of the tubular member (4).

3. The device as claimed in claim 1, wherein said mouthpiece (2) is substantially hollow, means (16) being provided in the hollow space inside said mouthpiece (2) for preventing the collapse of said space under the effect of underpressure applied by said vacuum source.

4. The device as claimed in claim 1, wherein at least one of said openings (8) is located in the center of said mouthpiece (2) and is of a size large enough to permit the passage therethrough of various implements.

5. The device as claimed in claim 1 wherein:

the mouthpiece is a pliable, pre-shaped, membranous material attached at selected points substantially along meridian lines, to a plurality of pre-shaped, finger-like elements (22), said elements having distal ends and proximal ends, the proximal ends of said finger-like elements (22) being connected to the tubular member (26) which is slidably located inside an outer tubular member 24), characterized in that said finger-like elements (22) exhibit different responses in different states, a first state response in which the distal ends of said finger-like elements (22) flex away from each other, thereby causing the pouch (20) to open and to engulf and entrap said specimen, and a second state response in which the distal ends of said finger-like elements (22) flex toward each other, thereby causing the pouch (20) to close, thereby retaining said specimen for retrieval.

6. The device as claimed in claim 5, wherein said finger-like elements (22) and said pouch (20) are accommodated prior to their use within said outer tubular member (24) with said pouch (20) being in a closely folded state, and when said tubular member (26) is pushed out of the outer member (24), the distal ends of said finger-like elements (22) flex away from each other, causing the pouch (20) to spread open.

7. A laparoscopic system for acquisition and retrieval of resected biological specimens, said system comprising:

at least three telescoping tubular members (4, 24, 26) having distal and proximal ends, including an outer tubular member (24), an inner tubular member (4) defining with said outer tubular member an annular space and being connectable at its proximal end to vacuum-producing means, and an intermediate tubular member (26) slidably fitting said outer tubular member;

a bowl-like mouthpiece (2) having a front face and a rear face, for capturing and retaining a resected specimen, said mouthpiece (2) being connected at its rear face to the distal end of said inner tubular member (4) and being made of an elastically resilient material, said mouthpiece (2) having a diameter in a non-deformed state exceeding the inside diameter of said outer tubular member (24) but fitting into the distal end of said outer tubular member by elastic deformation;

a plurality of finger-like elements (22) fixedly connected to the distal end of said intermediate tubular member (26);

a pouch (20) made of pliable, membraneous material fixedly attached at a plurality of points to said plurality of finger-like elements (22);

characterized in that, in the non-active, telescoped state of said system, said pouch (20), connected to said plurality of finger-like elements (22), is collapsed and disposed inside said annular space behind the rear face of said mouthpiece (2), and in the active state of said system, when said intermediate tubular member (26) is pushed out of the outer tubular member (24), the distal ends of said finger-like elements (22) first flex away from each other, thereby causing the pouch (20) to open and to engulf said mouthpiece (2), and thereafter, the distal ends of said finger-like elements (22) flex toward each other, thereby causing the pouch (20) to close, entrapping and retaining said specimen for retrieval.

8. The system as claimed in claim 7, wherein said finger-like elements (22) are made of a shaped-memory material exhibiting different responses to different temperatures.

9. The system as claimed in claim 8, wherein said different temperatures include a first temperature being the room temperature and a second temperature being at least the temperature inside a body, and wherein the response of the distal ends of said finger-like elements (22) to said first temperature is to spread out, while their response to said second temperature is to close.

10. The system as claimed in claim 8, wherein said shaped-memory material is a nickel-titanium alloy.

11. The system as claimed in claim 7, wherein said mouthpiece (2) is provided with a central opening for the introduction of a morcellator or a suction needle.

12. A method for acquisition and retrieval of resected biological specimens, using the system as claimed in claim 7, the method comprising the steps of:

introducing the distal end of the telescoped device into the body cavity;

pushing out the inner tubular member (4), thereby removing the mouthpiece (2) from the outer tubular member (24) and causing said mouthpiece (2) to assume its full diameter;

actuating the vacuum-producing means and moving mouthpiece (2) to a location in close proximity to the specimen to be resected, causing the resected specimen to cling to said mouthpiece (2);

pushing out the intermediate tubular member (26), thereby causing the distal ends of finger-like elements (22) to emerge from the annular space between the outer tubular member (24) and the inner member (4), said finger-like elements (22) carrying along and opening up the pouch (20) attached to them for engulfing the specimen retained by said mouthpiece (2);

allowing the distal ends of said finger-like elements (22) to close over said mouthpiece (2), thereby closing the pouch (20) over said specimen, and withdrawing the device from the body cavity.

13. The method as claimed in claim 12, wherein said specimen is removed from said body cavity by suction.

14. The method as claimed in claim 13, comprising the further step of introducing a surgical instrument (30) into said pouch (20) for the fragmentation of said specimen.

15. The method as claimed in claim 13, comprising the further step of introducing a suction needle into said pouch (20) for the evacuation of a liquefied specimen.

* * * * *